US012697367B2

(12) United States Patent
Furukawa et al.

(10) Patent No.: US 12,697,367 B2
(45) Date of Patent: Aug. 4, 2026

(54) MEDICAMENT FOR IMPROVING OR PREVENTING SYMPTOMS RELATING TO RETINA AND/OR LIGHT RECEPTION AND METHOD FOR SCREENING FOR SUBSTANCE CAPABLE OF IMPROVING OR PREVENTING SYMPTOMS RELATING TO RETINA AND/OR LIGHT RECEPTION

(71) Applicant: Osaka University, Osaka (JP)

(72) Inventors: Takahisa Furukawa, Osaka (JP); Taro Chaya, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 678 days.

(21) Appl. No.: 17/282,560

(22) PCT Filed: Oct. 11, 2019

(86) PCT No.: PCT/JP2019/040177
§ 371 (c)(1),
(2) Date: Apr. 2, 2021

(87) PCT Pub. No.: WO2020/080275
PCT Pub. Date: Apr. 23, 2020

(65) Prior Publication Data

US 2021/0338770 A1 Nov. 4, 2021

(30) Foreign Application Priority Data

Oct. 15, 2018 (JP) ................................ 2018-194648

(51) Int. Cl.

| | |
|---|---|
| ***A61K 38/13*** | (2006.01) |
| ***A61K 31/436*** | (2006.01) |
| ***A61P 27/02*** | (2006.01) |
| ***C12Q 1/44*** | (2006.01) |
| ***C12Q 1/48*** | (2006.01) |
| ***G01N 33/50*** | (2006.01) |

(52) U.S. Cl.
CPC ............ *A61K 38/13* (2013.01); *A61K 31/436* (2013.01); *A61P 27/02* (2018.01); *C12Q 1/44* (2013.01); *C12Q 1/485* (2013.01); *G01N 33/502* (2013.01)

(58) Field of Classification Search
None
See application file for complete search history.

(56) References Cited

U.S. PATENT DOCUMENTS

| | | | |
|---|---|---|---|
| 6,864,232 B1 | 3/2005 | Ueno | |
| 2004/0121968 A1 | 6/2004 | Ljubimov et al. | |
| 2005/0187241 A1 | 8/2005 | Wen et al. | |
| 2009/0036479 A1 | 2/2009 | Wen et al. | |
| 2009/0092665 A1 | 4/2009 | Mitra et al. | |
| 2009/0324689 A1* | 12/2009 | Cooper | A61P 9/10 424/428 |
| 2011/0300195 A1 | 12/2011 | Mitra et al. | |
| 2012/0190705 A1 | 7/2012 | Wen et al. | |
| 2013/0345185 A1 | 12/2013 | Mitra et al. | |
| 2015/0157687 A1 | 6/2015 | Mitra et al. | |
| 2020/0009217 A1 | 1/2020 | Mitra et al. | |
| 2020/0016229 A1 | 1/2020 | Furukawa | |

FOREIGN PATENT DOCUMENTS

| | | |
|---|---|---|
| JP | 2002-542150 A | 12/2002 |
| JP | 2010-540682 A | 12/2010 |
| JP | 2011-001380 A | 1/2011 |
| WO | WO 00/38703 A1 | 7/2000 |
| WO | WO 2004/027027 A2 | 4/2004 |
| WO | WO 2007/019427 A2 | 2/2007 |
| WO | WO 2010/120838 A1 | 10/2010 |
| WO | WO 2018/114557 A1 | 6/2018 |
| WO | WO 2018/169090 A1 | 9/2018 |

OTHER PUBLICATIONS

Safarini et al., "Caclineurin Inhibitors," NCBI Bookshelf, Nat. Inst. Health, StatPearls Publishing (last updated 2023) (Year: 2023).*
"Calcineuin inhibitors," Drugs.com, available online at www.drugs.com/drug-class/calcineurin-inhibitors.html, 2 pages (accessed on Dec. 8, 2023) (Year: 2023).*
MedChemExpress, "Casein Kinase", MedChemExpress, available online at www.medchemexpress.com/Targets/Casein%20Kinase.html?effectName=Activator, 2 pages (accessed on Dec. 11, 2023)) (Year: 2023).*
Sayed et al., J. Biol. Chem. 275:16569-16573 (2000) (Year: 2000).*
"Inhibit", The Britannica Dictionary, available online at /www.britannica.com/dictionary/inhibit, 1 page (accessed on Dec. 11, 2023) (Year: 2023).*
"Protect", Cambridge Dictionary, available online at https://dictionary.cambridge.org/us/dictionary/english/protect, 10 pages (accessed on Dec. 11, 2023) (Year: 2023).*
Seltman W., "Age-Related Macular Degeneration Diagnosis and Treatment," WebMD.com, available online at www.webmd.com/eye-health/macular-degeneration/age-related-macular-degeneration-treatment, 3 pages (2022) (Year: 2022).*

(Continued)

*Primary Examiner* — Thea D' Ambrosio
(74) *Attorney, Agent, or Firm* — Knobbe Martens Olson & Bear LLP

(57) ABSTRACT

The present invention provides a medicament for improving or preventing a symptom relating to a retina and/or light reception, the medicament comprising, as an active ingredient, a substance capable of maintaining or enhancing the phosphorylation state of Unc119; a method for screening for a substance capable of improving or preventing a symptom relating to a retina and/or light reception, the method comprising the step of selecting a substance capable of inhibiting calcineurin, or selecting a substance capable of activating casein kinase 2; and an agent for inhibiting retinal degeneration and an agent for protecting a retina, the agents each comprising, as an active ingredient, a substance capable of maintaining or enhancing the phosphorylation state of Unc119.

3 Claims, 6 Drawing Sheets

(56) References Cited

OTHER PUBLICATIONS

Jhu, "Age-Related Macular Degeneration (AMD)," JHU, available online at www.hopkinsmedicine.org/health/conditions-and-diseases/agerelated-macular-degeneration-amd, 5 pages (accessed on Dec. 5, 2023) (Year: 2023).*
Contin et al., Eye 30:255-263 (2016) (Year: 2016).*
Bhutto et al., Mol. Aspects Med. 33:295-317 (2012) (Year: 2012).*
Ambati et al., Neuron 75:26-39 (2012) (Year: 2012).*
Merck Manuals, "Drug Administration," Merck Manuals, available online at https://www.merckmanuals.com/home/drugs/administration-and-kinetics-of-drugs/drug-administration, 7 pages (last revised 2024) (Year: 2024).*
Medical dictionary, "Treat", Medical dictionary, available online at https://medical-dictionary.thefreedictionary.com/treat, 3 pages ( 2022) (Year: 2022).*
Kobayashi et al., Invest. Ophthalmol. Visual Sci. 41:3268-3277 (2000) (Year: 2000).*
Chaya, Taro et al., "Cul3-Klhl18 ubiquitin ligase modulates rod transducin translocation during light-dark adaptation" The EMBO Journal, Dec. 2019, pp. 1-22, vol. 38, No. 23, e101409.
Furukawa, T. et al., "Ubiquitin-dependent regulation of transducin translocation during light and dark adaptation" 2019 Annual Meeting Association for Research in Vision and Ophthalmology, ARVO 2019, Jul. 2019.
Supplementary European Search Report for EP 19873926 dated Jan. 24, 2022.
Decision of Rejection in CN 201980067988.4 issued Jun. 30, 2023.
Liming, Peng et al., "Basic and Clinical Apoptosis", People's Health Publishing House, 2007, pp. 527-528.
First Office Action for JP 2020-553143 dated Aug. 8, 2023.
Office Action for CN 201980067988.4 issued Jul. 4, 2022.
Office Action for CN 201980067988.4 issued Jan. 18, 2023.
Apr. 14, 2021 Int'l Preliminary Report on Patentability from PCT/JP2019/040177 (10 pgs).
Communication pursuant to Article 94(3) EPC issued in EP 19873926.0 dated Jun. 25, 2024.
Gil-Martinez et al., "Pharmacological Advances in the Treatment of Age-related Macular Degeneration", Current Medicinal Chemistry, 2020, vol. 27, No. 4, pp. 583-598.
Varela-Fernández et al., "Drug Delivery to the Posterior Segment of the Eye: Biopharmaceutic and Pharmacokinetic Considerations", Pharmaceutics, 2020, pp. 1-39.
Fujiyama-Nakamura, Sally et al., "BTB protein, dKLHL18CG3571, serves as an adaptor subunit for a dCul3 ubiquitin ligase complex" Genes to Cells, 2009, pp. 965-973, vol. 14.
Ishiba, Yasutsugu et al., "Targeted inactivation of synaptic HRG4 (UNC1119) causes dysfunction in the distal photoreceptor and slow retinal degeneration, revealing a new function" Experimental Eye Research, 2007, pp. 473-485, vol. 84.
Kobayashi, Akira et al., "HRG4 (UNC119) Mutation Found in Cone-Rod Dystrophy Causes Retinal Degeneration in a Transgenic Model" IOVS, Oct. 2000, pp. 3268-3277, vol. 41, No. 11.
Kramerov, Andrei A., et al., "Expression of Protein Kinase CK2 in Astroglial Cells of Normal and Neovascularized Retina" American Journal of Pathology, May 2006, pp. 1722-1736, vol. 168, No. 5.
Moghe, Saili et al., "The CUL3-KLHL18 ligase regulates mitotic entry and ubiquitylates Aurora-A" Biology Open, 2012, pp. 82-91, vol. 1.
International Search Report for PCT/JP2019/040177 dated Nov. 12, 2019.
Communication pursuant to Article 94(3) EPC received in European Patent Application No. 19873926.0, dated Feb. 5, 2026.

* cited by examiner

Thickness of photoreceptor layer

- - - - Control (DMSO): no light-induced damage
- - - - Control (DMSO): light-induced damage
━━━━ Tacrolimus administration: no light-induced damage
· · · · · · · Tacrolimus administration: light-induced damage Thickness of photoreceptor layer

- – – Control (DMSO): no light-induced damage
- ═ ═ Control (DMSO): light-induced damage
- ▬▬▬ Ciclosporin administration: no light-induced damage
- ‹‹‹‹‹ Ciclosporin administration: light-induced damage

In vitro kinase assay

CK2:     —        +

6His-Unc119

MEDICAMENT FOR IMPROVING OR PREVENTING SYMPTOMS RELATING TO RETINA AND/OR LIGHT RECEPTION AND METHOD FOR SCREENING FOR SUBSTANCE CAPABLE OF IMPROVING OR PREVENTING SYMPTOMS RELATING TO RETINA AND/OR LIGHT RECEPTION

CROSS REFERENCE TO RELATED APPLICATIONS

This application is a U.S. National Phase Application of PCT International Application Number PCT/JP2019/040177, filed on Oct. 11, 2019, designating the United States of America and published in the Japanese language, which is an International Application of and claims the benefit of priority to Japanese Patent Application No. 2018-194648, filed on Oct. 15, 2018. The disclosures of the above-referenced applications are hereby expressly incorporated by reference in their entireties.

TECHNICAL FIELD

The present invention relates to a medicament for improving or preventing a symptom relating to a retina and/or light reception, and a method for screening for a substance capable of improving or preventing a symptom relating to a retina and/or light reception.

BACKGROUND ART

The retina is the central nerve tissue that receives optical information from the external world. More than 80% of information in the external world humans acquired is processed visually. Some diseases that cause visual impairment currently have no curative treatment, and typical examples of such diseases are retinal degeneration diseases. Retinal degeneration is characterized by irreversible loss of visual function due to loss of photoreceptor cells. Retinal degeneration is caused by retinitis pigmentosa and macular degeneration (dry type), which are the third and fourth leading causes of blindness in Japan, respectively. These diseases affect a large number of people and cause severe visual impairment, and thus development of preventive and curative treatments is desired. Retinitis pigmentosa and age-related macular degeneration are also the leading causes of blindness in the world. Mechanisms of progression of the pathological conditions of such retinal degeneration diseases vary and involve several factors including heredity, aging and environment, but these diseases share a common phenotype: death of photoreceptor cells. Long-term exposure to light induces accumulation of metabolic waste products and cell stress, and causes aging and cell death of photoreceptor cells and retinal pigment epithelium, leading to the onset and exacerbation of retinal degeneration diseases, including age-related macular degeneration and retinitis pigmentosa. This phenomenon is well known as light-induced damage, and damage caused by blue light emitted from a computer display or other devices has recently attracted attention. Reduction of light-induced damage due to long-term exposure to light is important for retinal protection and inhibition of progression of retinal degeneration.

The inventors identified that a ubiquitinating enzyme is predominantly expressed in the retina, and found that this enzyme modulates light and dark adaptation (light response sensitivity) of retinal photoreceptor cells based on the analysis of mice with knockout of the enzyme (Patent literature 1). The molecular mechanisms of light and dark adaptation in photoreceptor cells are largely unknown. However, if a new molecular mechanism of light and dark adaptation via protein ubiquitination in photoreceptor cells is clarified from functional analysis of ubiquitinating enzymes in the retina, such discovery is expected to lead to development of a new progression inhibitor for retinitis pigmentosa or age-related macular degeneration based on a completely new molecular mechanism.

CITATION LIST

Patent Literature

Patent literature 1: WO 2018/169090

SUMMARY OF INVENTION

Technical Problem

An object of the present invention is to provide a medicament for improving or preventing a symptom relating to a retina and/or light reception. Another object of the present invention is to provide a method for screening for a substance capable of improving or preventing a symptom relating to a retina and/or light reception. A further another object of the present invention is to provide an agent for inhibiting retinal degeneration due to light exposure and an agent for protecting a retina.

Solution to Problem

The present invention was made to solve the above problems and includes the following.

(1) A medicament for improving or preventing a symptom relating to a retina and/or light reception, the medicament comprising, as an active ingredient, a substance capable of maintaining or enhancing the phosphorylation state of Unc119.

(2) The medicament according to the above (1), wherein the substance capable of maintaining or enhancing the phosphorylation state of Unc119 is a calcineurin inhibitor or a casein kinase 2 activator.

(3) The medicament according to the above (2), wherein the calcineurin inhibitor is ciclosporin or tacrolimus.

(4) The medicament according to the above (3), wherein the symptom relating to a retina and/or light reception is at least one disease selected from the group consisting of age-related macular degeneration, retinitis pigmentosa, Leber congenital amaurosis, Stargardt disease, cone-rod dystrophy, diabetic retinopathy, macular edema, retinal ischemia, retinal artery occlusion, retinal vein occlusion, photosensitive seizure, photosensitive epilepsy, psychiatric disorders, photic maculopathy, asthenopia, retinal dysfunction, sleep disorders, migraine, and light-induced damage.

(5) The medicament according to the above (4), wherein the symptom relating to a retina and/or light reception is at least one disease selected from the group consisting of age-related macular degeneration, retinitis pigmentosa, Leber congenital amaurosis, Stargardt disease, cone-rod dystrophy, diabetic retinopathy, macular edema, retinal ischemia, retinal artery occlusion, retinal vein occlusion, photic maculopathy, asthenopia, retinal dysfunction, and light-induced damage.

(6) A method for screening for a substance capable of improving or preventing a symptom relating to a retina and/or light reception, the method comprising the step of selecting a substance capable of inhibiting calcineurin.

(7) The screening method according to the above (6), which comprises the steps of:

contacting each of a plurality of test substances with calcineurin, calmodulin and Unc119, determining the phosphorylation state of Unc119, and selecting a test substance capable of enhancing the phosphorylation state of Unc119 as compared with the phosphorylation state of Unc119 in the absence of contact with the test substance.

(8) The screening method according to the above (7), wherein the step of contacting each of a plurality of test substances with calcineurin, calmodulin and Unc119 is performed by contacting each of a plurality of test substances with a cell expressing calcineurin, calmodulin and Unc119.

(9) The screening method according to the above (6), which comprises the steps of:

contacting each of a plurality of test substances with calcineurin, calmodulin and Unc119, determining the level of interaction between calcineurin and Unc119, and selecting a test substance capable of reducing the level of interaction between calcineurin and Unc119 as compared with the level of interaction between calcineurin and Unc119 in the absence of contact with the test substance.

(10) A method for screening for a substance capable of improving or preventing a symptom relating to a retina and/or light reception, the method comprising the step of selecting a substance capable of activating casein kinase 2.

(11) The screening method according to the above (10), which comprises the steps of:

contacting each of a plurality of test substances with casein kinase 2 and Unc119 in the presence of ATP, determining the phosphorylation state of Unc119, and selecting a test substance capable of enhancing the phosphorylation state of Unc119 as compared with the phosphorylation state of Unc119 in the absence of contact with the test substance.

(12) The screening method according to the above (11), wherein the step of contacting each of a plurality of test substances with casein kinase 2 and Unc119 in the presence of ATP is performed by contacting each of a plurality of test substances with a cell expressing casein kinase 2 and Unc119 in the presence of ATP.

(13) An agent for inhibiting retinal degeneration, the agent comprising, as an active ingredient, a substance capable of maintaining or enhancing the phosphorylation state of Unc119.

(14) The agent for inhibiting retinal degeneration according to the above (13), wherein retinal degeneration is accompanied by at least one selected from structural destruction of cone photoreceptor cells due to light exposure, structural destruction of rod photoreceptor cells due to light exposure, and reduction in thickness of a photoreceptor layer due to light exposure.

(15) An agent for protecting a retina, the agent comprising, as an active ingredient, a substance capable of maintaining or enhancing the phosphorylation state of Unc119.

Advantageous Effects of Invention

The present invention provides a medicament for improving or preventing a symptom relating to a retina and/or light reception. The medicament may comprise as an active ingredient a calcineurin inhibitor that is already clinically applied, and is thus highly safe. The screening method of the present invention can identify a substance useful for improvement or prevention of a symptom relating to a retina and/or light reception, and the identified substance can be formulated into a medicament for improving or preventing a symptom relating to a retina and/or light reception. The present invention also provides an agent for inhibiting retinal degeneration due to light exposure and an agent for protecting a retina.

DESCRIPTION OF EMBODIMENTS

Figure 1:
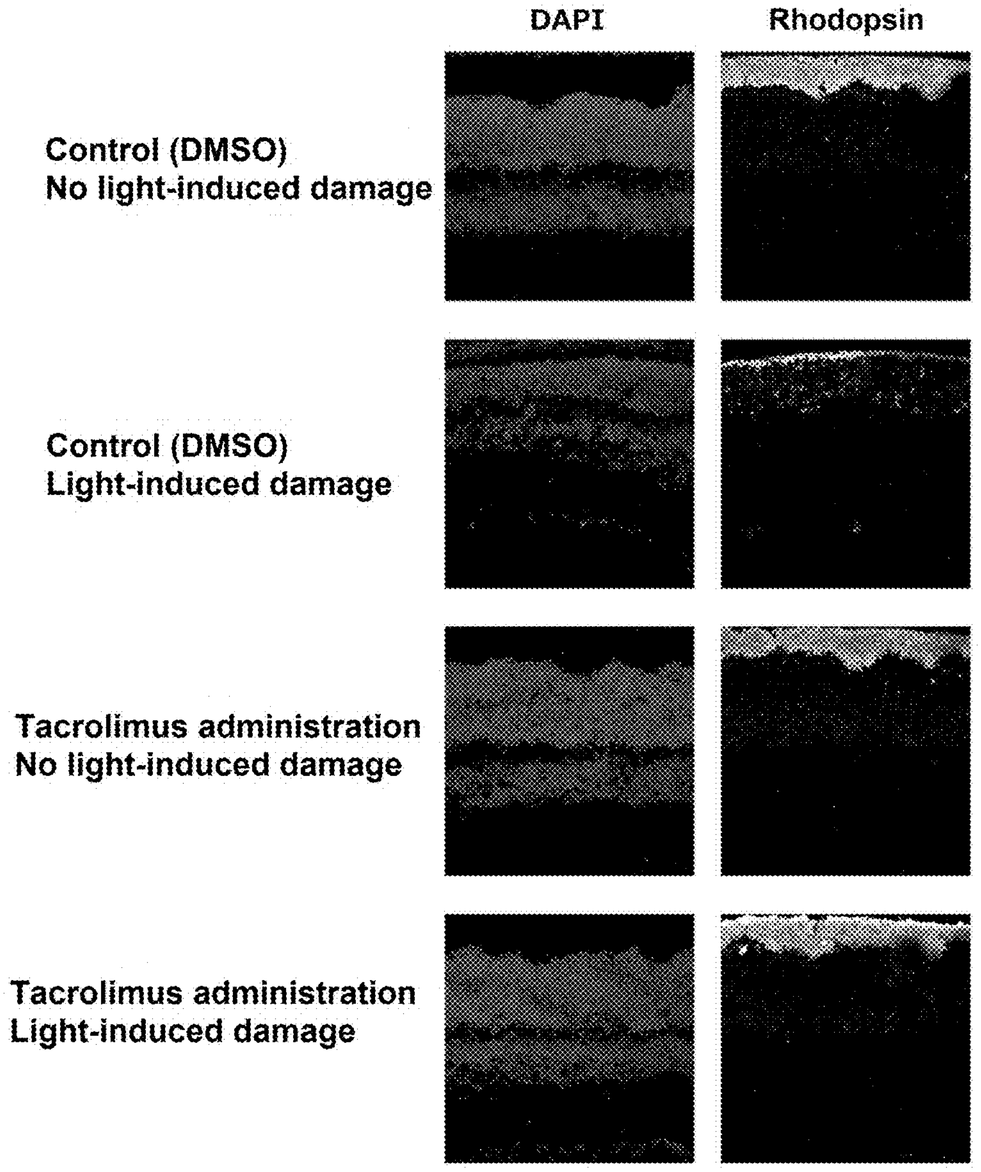
FIG. 1 shows fluorescence immunostaining of the outer segment of rod photoreceptor cells in the retina of tacrolimus-administered mice with light-induced damage.

The inventors identified that Klhl18, a ubiquitinating enzyme, is predominantly expressed in the retina, and found that Klhl18 modulates light and dark adaptation (light response sensitivity) of retinal photoreceptor cells based on the analysis of Klhl18 knockout mice (Patent literature 1). The inventors also found that Klhl18 targets Unc119 protein, and degradation of the target protein is regulated by the phosphorylation and dephosphorylation of the target protein. The inventors further identified that the phosphorylation of Unc119 is catalyzed by casein kinase 2 enzyme (also called CK2), and the dephosphorylation of Unc119 is catalyzed by calcineurin enzyme.

Medicament

The present invention provides a medicament for improving or preventing a symptom relating to a retina and/or light reception, the medicament comprising, as an active ingredient, a substance capable of maintaining or enhancing the phosphorylation state of Unc119. The term "symptom" as used herein includes diseases etc. The term "improvement" as used herein includes treatment etc., and the degree of improvement is not limited to a particular one. The "improvement" also includes remission of a symptom and complete recovery from a symptom, etc. The term "prevention" is used to mean to include inhibition of onset and progression of a symptom, and the degree of prevention is not limited to a particular one.

The substance capable of maintaining or enhancing the phosphorylation state of Unc119 may be a substance capable of inhibiting the dephosphorylation of phosphorylated Unc119, or a substance capable of enhancing the phosphorylation of Unc119. Dephosphorylation of Unc119 is catalyzed by calcineurin enzyme, and therefore the substance capable of inhibiting the dephosphorylation of phosphorylated Unc119 may be a calcineurin inhibitor. Any known calcineurin inhibitor can be appropriately used as the calcineurin inhibitor. The known calcineurin inhibitor may be ciclosporin or tacrolimus. Phosphorylation of Unc119 is catalyzed by CK2 enzyme, and therefore the substance capable of enhancing the phosphorylation of Unc119 may be a CK2 activator.

Ciclosporin is a well-known active ingredient used as an immunosuppressant. This active ingredient has been approved as an ethical pharmaceutical in Japan, and has been registered in the National Health Insurance Price List. Ciclosporin is also called cyclosporin, ciclosporin A, cyclosporin A, or CsA. Ciclosporin is listed in the Japanese pharmacopoeia, and described in the Japanese pharmacopoeia as follows.

Generic name: ciclosporin, Alternative name: cyclosporin A Chemical name: cyclo{-[(2S,3R,4R,6E)-3-Hydroxy-4-methyl-2-methylaminooct-6-enoyl]-L-2-aminobutanoyl-N-methylglycyl-N-methyl-L-leucyl-L-valyl-N-methyl-L-leucyl-L-alanyl-D-alanyl-N-methyl-L-leucyl-N-methyl-L-leucyl-N-methyl-L-valyl-}

Molecular formula: $C_{62}H_{111}N_{11}O_{12}$

Molecular weight: 1202.61

Structural formula:

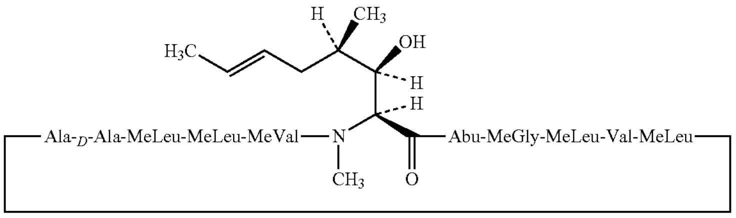

Abu = (2S)-2-Aminobutyric acid
MeGly = N-Methylglycine
MeLeu = N-Methylleucine
MeVal = N-Methylvaline Tacrolimus is a well-known active ingredient used as an immunosuppressant. This active ingredient has been approved as an ethical pharmaceutical in Japan, and has been registered in the National Health Insurance Price List. Tacrolimus is also called FK506. Tacrolimus is listed as tacrolimus hydrate in the Japanese pharmacopoeia, and tacrolimus used in the present invention may be tacrolimus hydrate. Tacrolimus hydrate is described in the Japanese pharmacopoeia as follows.

Generic name: Tacrolimus Hydrate

Chemical name:

(3S,4R,5S,8R,9E,12S,14S,15R,16S,18R,19R,26aS)-5,19-Dihydroxy-3-{(1E)-2-[(1R,3R,4R)-4-hydroxy-3-methoxycyclohexyl]-1-methylethenyl}-14,16-dimethoxy-4,10,12,18-tetramethyl-8-(prop-2-en-1-yl)-15,19-epoxy-5,6,8,11,12,13,14,15,16,17,18,19,24,25,26,26a-hexadecahydro-3H-pyrido[2,1-c][1,4]oxaazacyclotricosine-1,7,20,21(4H,23H)-tetrone monohydrate Molecular formula: $C_{44}H_{69}NO_{12}.H_2O$ Molecular weight: 822.03

Structural formula:

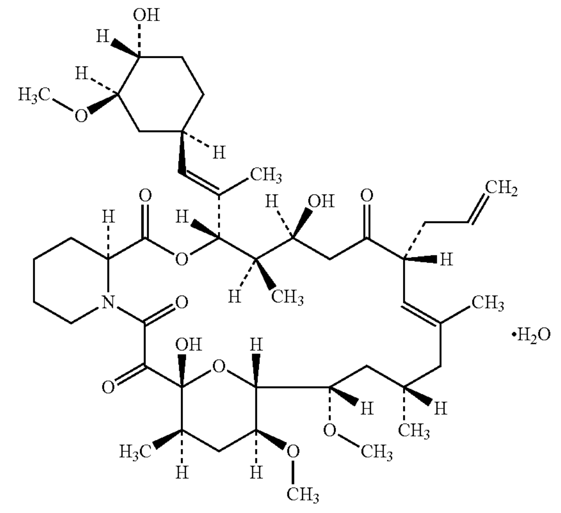

The symptom relating to a retina and/or light reception may be a symptom expressed in the retina, or a symptom expressed in an internal organ or tissue other than the retina. The symptom expressed in the retina may be a symptom expressed in the retina as a result of an abnormality in the retina, or a symptom expressed in the retina as a result of an abnormality in an internal organ or tissue other than the retina. The symptom expressed in an internal organ or tissue other than the retina is limited to a symptom as a result of an abnormality in the retina. The symptom as a result of an abnormality in the retina may be, for example, a symptom caused by photic stimulation or photostress in daily life, or a symptom caused by exposure to strong light.

Examples of the symptom relating to a retina and/or light reception include age-related macular degeneration, retinitis pigmentosa, Leber congenital amaurosis, Stargardt disease (juvenile macular degeneration), cone-rod dystrophy, diabetic retinopathy, macular edema, retinal ischemia, retinal artery occlusion, retinal vein occlusion, photosensitive seizure, photosensitive epilepsy, psychiatric disorders, photic maculopathy, asthenopia, retinal dysfunction (for example, due to aging etc.), sleep disorders, migraine, light-induced damage (for example, light-induced damage caused by outdoor activities, sports, or mountaineering under the sun or caused by blue light emitted from computer displays, etc.), hyperesthesia, and psychiatric disorders accompanied by visual cognitive impairment (for example, depression, depressive state, bipolar disorder (manic depression), autism, mental development disorder, schizophrenia, etc.). Examples of the symptom expressed in the retina include age-related macular degeneration, retinitis pigmentosa, Leber congenital amaurosis, Stargardt disease, cone-rod dystrophy, diabetic retinopathy, macular edema, retinal ischemia, retinal artery occlusion, retinal vein occlusion, photic maculopathy, asthenopia, retinal dysfunction, and light-induced damage.

The medicament for improving or preventing a symptom relating to a retina and/or light reception according to the invention can also be called a medicament for protecting a retina, a medicament for inhibiting retinal degeneration, a medicament for inhibiting aging of a retina, a medicament for improving or inhibiting hyperesthesia, a medicament for improving or preventing a light-induced disease, or a medicament for improving or preventing a light-induced disorder.

The medicament of the present invention can be formulated by combining the active ingredient with a pharmaceutically acceptable carrier and, if necessary, an additive. Specifically, the medicament can be formulated into an oral formulation, such as a tablet, a coated tablet, a pill, a powder, granules, a capsule, a liquid, a suspension and an emulsion; or a parenteral formulation, such as an injection, an infusion, a suppository, an ointment and a patch. The blending ratio of a carrier or additive is determined as appropriate based on the range usually employed in the pharmaceutical field. The carrier or additive that can be combined is not limited to a particular one, and examples thereof include various types of carriers, such as water, physiological saline, other aqueous solvents, aqueous or oily bases; and various types of additives such as excipients, binders, pH adjusting agents, disintegrants, absorption enhancers, lubricants, colorants, flavor improvers and fragrances.

Examples of the excipients include, but are not limited to, lactose, sucrose, D-mannitol, starch, crystalline cellulose, and light anhydrous silicic acid. Examples of the binders include, but are not limited to, high molecular weight compounds, such as crystalline cellulose, sucrose, D-mannitol, dextrin, hydroxypropyl cellulose, hydroxypropyl methylcellulose, and polyvinylpyrrolidone. Examples of the lubricants include, but are not limited to, magnesium stearate, calcium stearate, talc, and colloidal silica. Examples of the disintegrants include, but are not limited to, starch, carboxymethyl cellulose, carboxymethylcellulose calcium, croscarmellose sodium, and carboxymethyl starch sodium. Examples of wetting agents include, but are not limited to, glycerol, butylene glycol, propylene glycol, sorbitol, and triacetin. If necessary, the formulation may be coated with a coating agent (e.g., sucrose, gelatin, hydroxypropyl cellulose, hydroxypropyl methylcellulose phthalate, etc.) or coated with two or more layers.

The medicament in the form of an injection for intravenous, intramuscular or subcutaneous administration can be prepared by dissolving or dispersing the active ingredient in an aqueous base such as physiological saline or an oily base acceptable for injection. If necessary, an additive, such as a buffering agent, a pH adjusting agent, an isotonic agent, a solubilizing agent, a suspending agent, or a stabilizer can be added as appropriate.

Examples of the aqueous base for preparing the injection include physiological saline, water for injection, and a solution for infusion such as Ringer's solution. Examples of the oily base include propylene glycol, polyethylene glycol, sesame oil, soybean oil, corn oil, peanut oil, cottonseed oil, olive oil, and propylene glycol fatty acid ester. Examples of the buffering agent include phosphates, acetates, carbonates, citrates, borates, glutamates, epsilon-aminocaproates, and buffers such as Tris buffer. Examples of the pH adjusting agent include inorganic acids, such as hydrochloric acid, phosphoric acid, sulfuric acid, and carbonic acid; organic acids, such as acetic acid, tartaric acid, lactic acid, citric acid, and succinic acid; inorganic bases, such as sodium hydroxide; and organic bases, such as sodium citrate and sodium tartrate. Examples of the isotonic agent include minerals, such as sodium chloride; sugar alcohols, such as D-mannitol, sorbitol, and xylitol; sugars, such as fructose, glucose, galactose, ribose, xylose, mannose, maltotriose, and maltotetraose; and amino acids, such as glycine and arginine. Examples of the solubilizing agent include polyethylene glycol, propylene glycol, D-mannitol, benzyl benzoate, ethanol, tris aminomethane, cholesterol, triethanolamine, sodium carbonate, sodium citrate, lecithin, and nonionic surfactants such as polysorbate 80. Examples of the suspending agent include surfactants, such as stearyltriethanolamine, sodium lauryl sulfate, lauryl amino propionate, lecithin, and glyceryl monostearate; and polyvinyl alcohol, polyvinylpyrrolidone, carboxymethyl cellulose sodium, methyl cellulose, and hydroxymethyl cellulose. Examples of the stabilizer include albumin, globulin, gelatin, sorbitol, ethylene glycol, propylene glycol, and ascorbic acid.

Ciclosporin and tacrolimus, which serve as the active ingredient of the medicament of the present invention, are substances that have already been used in the clinical setting over many years. Therefore the medicament of the present invention can be safely administered to humans or other mammals (for example, rats, mice, rabbits, sheep, pigs, cattle, cats, dogs, monkeys, etc.).

The daily dosage of the medicament of the present invention comprising ciclosporin or tacrolimus as an active ingredient can be determined in accordance with the clinically applied daily dosage of ciclosporin or tacrolimus.

Agent for Inhibiting Retinal Degeneration and Agent for Protecting Retina

The present invention provides an agent for inhibiting retinal degeneration, the agent comprising, as an active ingredient, a substance capable of maintaining or enhancing the phosphorylation state of Unc119. The present invention also provides an agent for protecting a retina, the agent comprising, as an active ingredient, a substance capable of maintaining or enhancing the phosphorylation state of Unc119. The inventors induced light-induced damage in mice that received tacrolimus or ciclosporin, and prepared cryosections of the retina and examined the photoreceptor layer of the retina under a confocal laser scanning microscope. The results demonstrate that the structure of the cone photoreceptor cells and the rod photoreceptor cells was not destroyed but maintained, and the thickness of the photoreceptor layer was also not reduced but maintained (see Example 1). Therefore, the agent for inhibiting retinal degeneration and the agent for protecting a retina according to the present invention are effective in prevention or treatment of light-induced damage.

The agent for inhibiting retinal degeneration and the agent for protecting a retina according to the present invention can comprise, as an active ingredient, any one of the substances described in the above embodiments of the medicament. The agent for inhibiting retinal degeneration and the agent for protecting a retina according to the present invention can be formulated into various types of dosage forms as described in the above embodiments of the medicament. The agent for inhibiting retinal degeneration and the agent for protecting a retina according to the present invention can be safely administered to humans or other mammals (for example, rats, mice, rabbits, sheep, pigs, cattle, cats, dogs, monkeys, etc.).

Screening Method

The present invention provides a method for screening for a substance capable of improving or preventing a symptom relating to a retina and/or light reception. The screening method of the present invention may be used to select a substance capable of inhibiting calcineurin, or may be used to select a substance capable of activating CK2. The substance capable of inhibiting calcineurin may be identified by selecting a substance capable of inhibiting the dephosphorylation of a substrate for calcineurin. The substance capable of activating CK2 may be identified by selecting a substance capable of enhancing the phosphorylation of a substrate for CK2.

The symptom relating to a retina and/or light reception according to the screening method of the present invention may be a symptom expressed in the retina, or a symptom expressed in an internal organ or tissue other than the retina. The symptom expressed in the retina may be a symptom expressed in the retina as a result of an abnormality in the retina, or a symptom expressed in the retina as a result of an abnormality in an internal organ or tissue other than the retina. The symptom expressed in an internal organ or tissue other than the retina is limited to a symptom related to light reception of the retina. Specific examples of the symptom relating to the retina and/or light reception include the symptoms as exemplified above.

A test substance to be subjected to the screening method of the present invention may be, for example, but is not limited to, a nucleic acid, a peptide, a protein, a non-peptidic compound, a synthetic compound, a fermentation product, a cell extract, a cell culture supernatant, a plant extract, a mammalian tissue extract, plasma, or the like. The test substance may be a novel substance or a known substance. The test substance may be in the form of a salt. The salt of the test substance is preferably a salt with a physiologically acceptable acid or base.

The screening method of the present invention may comprise the step of selecting a substance capable of inhibiting calcineurin. In an embodiment where the substance capable of inhibiting calcineurin is a substance capable of inhibiting the dephosphorylation of a substrate for calcineurin, the screening method of the present invention may comprise, for example, the steps of:

contacting each of a plurality of test substances with calcineurin, calmodulin and a substrate for calcineurin, determining the phosphorylation state of the substrate, and selecting a test substance capable of enhancing the phosphorylation state of the substrate as compared with the phosphorylation state of the substrate in the absence of contact with the test substance.

The screening method of the present invention may also comprise, for example, the steps of:

contacting each of a plurality of test substances with calcineurin, calmodulin and a substrate for calcineurin, determining the level of interaction between calcineurin and the substrate, and selecting a test substance capable of reducing the level of interaction between calcineurin and the substrate as compared with the level of interaction between calcineurin and the substrate in the absence of contact with the test substance.

The substrate for calcineurin may be any one selected from known substrates for calcineurin. Examples of the substrate for calcineurin include, but are not limited to, NFATC1 (nuclear factor of activated T cells 1) and DNM1 (dynamin 1). Preferably, the substrate for calcineurin is Unc119, which is a target protein of K1h118, a ubiquitinating enzyme predominantly expressed in the retina. The screening method of the present invention according to an embodiment where the substrate for calcineurin is Unc119 will be described in detail below, but the screening method using a substrate other than Unc119 can also be performed in the same manner as described below.

The screening method of the present invention may comprise the steps of:

contacting each of a plurality of test substances with calcineurin, calmodulin and Unc119, determining the phosphorylation state of Unc119, and selecting a test substance capable of enhancing the phosphorylation state of Unc119 as compared with the phosphorylation state of Unc119 in the absence of contact with the test substance.

The step of contacting each of a plurality of test substances with calcineurin, calmodulin and Unc119 may be performed by preparing a solution containing calcineurin, calmodulin and Unc119 and adding each of test substances to the solution, or alternatively, by culturing cells expressing calcineurin, calmodulin and Unc119 and adding each of test substances to the culture medium.

Calcineurin used in the screening method of the present invention may be from any organism, and may be from a mammal. Examples of the mammal include humans, chimpanzees, monkeys, dogs, cattle, mice, rats, and guinea pigs. Preferred is human calcineurin. Calcineurin may be recombinant calcineurin that is commercially available as a reagent, recombinant calcineurin included in a commercially available kit (for example, Calcineurin cellular activity assay kit by Enzo Life Sciences, Inc.), or recombinant calcineurin produced by a known genetic engineering technique.

Calcineurin (also called protein phosphatase 2B (PP2B) or protein phosphatase 3 (ppp3)) is a heterodimer composed of a catalytic calcineurin A subunit and a regulatory calcineurin B subunit. Calcineurin is activated when bound to calmodulin. Calcineurin-expressing cells can be prepared by introducing a gene encoding calcineurin A and a gene encoding calcineurin B into appropriate host cells. The prepared calcineurin-expressing cells are cultured, and the culture supernatant or the cell extract is purified by a known method (for example, using an affinity column) to produce recombinant calcineurin.

The accession Nos. of the amino acid sequences of human calcineurin A and calcineurin B and the nucleotide sequences of the genes encoding the amino acid sequences are shown in Table 1. Calcineurin A selected from PPP3CA, PPP3CB and PPP3CC and calcineurin B selected from PPP3R1 and PPP3R2, each shown in Table 1, can be introduced into host cells to produce calcineurin-expressing cells. Information on the nucleotide sequences and amino acid sequences of calcineurin A and calcineurin B of organisms other than humans is available from known databases (DDBJ, GenBank, EMBL, etc.).

TABLE 1

| Subunit | Gene name | Nucleotide sequence | Amino acid sequence |
|---|---|---|---|
| Calcineurin A | PPP3CA | NM_000944 | NP_000935 |
| | PPP3CB | NM_001142353 | NP_001135825 |
| | PPP3CC | NM_001243974 | NP_001230903 |
| Calcineurin B | PPP3R1 | NM_000945 | NP_000936 |
| | PPP3R2 | NM_147180 | NP_671709 |

Calmodulin used in the screening method of the present invention may be from any organism, and may be from a mammal. Examples of the mammal include humans, chimpanzees, monkeys, dogs, cattle, mice, rats, and guinea pigs. Preferred is human calmodulin. Calmodulin may be recombinant calmodulin that is commercially available as a reagent, recombinant calmodulin included in a commercially available kit (for example, Calcineurin cellular activity assay kit by Enzo Life Sciences, Inc.), or recombinant calmodulin produced by a known genetic engineering technique.

Human calmodulin includes three family members: calmodulin 1, calmodulin 2 and calmodulin 3. Calmodulin-expressing cells can be prepared by introducing a gene encoding any one of these family members into appropriate host cells. The prepared calmodulin-expressing cells are cultured, and the culture supernatant or the cell extract is purified by a known method (for example, using an affinity column) to produce recombinant calmodulin. The accession Nos. of the amino acid sequences of human calmodulin 1, 2 and 3 and the nucleotide sequences of the genes encoding the amino acid sequences are shown in Table 2. Information on the nucleotide sequences and amino acid sequences of calmodulin of organisms other than humans is available from known databases (DDBJ, GenBank, EMBL, etc.).

TABLE 2

| | Gene name | Nucleotide sequence | Amino acid sequence |
|---|---|---|---|
| Calmodulin 1 | CALM1 | NM_006888 | NP_008819 |
| Calmodulin 2 | CALM2 | NM_001743 | NP_001734 |
| Calmodulin 3 | CALM3 | NM_005184 | NP_005175 |

Unc119 used in the screening method of the present invention may be from any organism, and may be from a mammal. Examples of the mammal include humans, chimpanzees, monkeys, dogs, cattle, mice, rats, and guinea pigs. Preferred is human Unc119. Unc119 may be recombinant Unc119 produced by a known genetic engineering technique. Unc119-expressing cells can be prepared by introducing a gene encoding Unc119 into host cells. The prepared Unc119-expressing cells are cultured, and the culture supernatant or the cell extract is purified by a known method (for example, using an affinity column) to produce recombinant Unc119.

The accession Nos. of the amino acid sequence of human Unc119 and the nucleotide sequence of the gene encoding the amino acid sequence are NM 005148 and NP 005139, respectively. Information on the nucleotide sequences and amino acid sequences of Unc119 of organisms other than humans is available from known databases (DDBJ, GenBank, EMBL, etc.).

The cells expressing calcineurin, calmodulin and Unc119 used in the screening method of the present invention may be cells expressing endogenous calcineurin, endogenous calmodulin and endogenous Unc119, cells expressing recombinant calcineurin, recombinant calmodulin and recombinant Unc119 each of which is derived from a transgene, or cells expressing calcineurin, calmodulin and Unc119 each of which may be an endogenous or recombinant protein. Preferred are cells expressing recombinant calcineurin, recombinant calmodulin and recombinant Unc119. The cells can be prepared by co-introducing a gene encoding calcineurin A, a gene encoding calcineurin B, a gene encoding calmodulin and a gene encoding Unc119 into host cells. The nucleotide sequences of the genes are as described above. The host cells are not limited and may be any cells capable of expressing the introduced gene products. Examples of the host cells include HEK 293T cells, Neuro 2a cells and NIH 3T3 cells. These cells can also be appropriately used as host cells for producing recombinant calcineurin-expressing cells, recombinant calmodulin-expressing cells, and recombinant Unc119-expressing cells.

In the step of contacting each of a plurality of test substances with calcineurin, calmodulin and Unc119, wherein a solution containing calcineurin, calmodulin and Unc119 is prepared and each of test substances is added to the solution, the amounts of calcineurin, calmodulin and Unc119 added to the solution are not limited to particular ones, but the molar ratio of calcineurin and calmodulin and Unc119 may be about 1:1:1. The amount of each of test substances added is not limited and may be any amount that allows determination of the phosphorylation state of Unc119 in the subsequent step. Each of test substances may be added at varying concentrations within a predetermined range.

The solution used is not limited and may be any known buffer that can appropriately be used for phosphorylation reaction of a protein. The buffer may be, for example, 50 mM Tris-HCl (pH 7.5) buffer containing 1 mM $CaCl_2$, 100 mM NaCl, 1 mg/ml BSA, 0.025% NP-40, and 1 mM DTT. The reaction conditions including the temperature of the solution and the duration of the contact may be any conditions that allow calcineurin and calmodulin to form a complex and catalyze the dephosphorylation of Unc119. For example, the temperature of the solution may be 37° C., and the duration of the contact may be 30 minutes.

In the step of contacting each of a plurality of test substances with calcineurin, calmodulin and Unc119, wherein cells expressing calcineurin, calmodulin and Unc119 are cultured, and each of a plurality of test substances is added to the culture medium, each of a plurality of test substances added to the culture medium may be in any amount that does not significantly inhibit proliferation of the cells and expression of the recombinant proteins. Each of test substances may be added at varying concentrations within a predetermined range. The duration of contact of each of test substances with the cells is not limited, and may be about 0.5 hours to about 48 hours.

In an embodiment where cells expressing calcineurin, calmodulin and Unc119 are used, a cell lysate is prepared for measurement of the level of phosphorylation of Unc119 and used in the subsequent step. The cell lysate may be prepared by any method selected from known methods as appropriate. Specifically, the cell lysate may be prepared, for example, as follows. The culture medium is removed, and the cells are washed twice with TBS (Tris-buffered saline: 20 mM Tris-HCl, pH 7.4 and 150 mM NaCl). The cells are lysed by pipetting in lysis buffer (20 mM Tris-HCl, pH 7.4, 150 mM NaCl, 1% NP-40, and phosphatase inhibitor cocktail (Roche)), and left to stand on ice for 10 minutes. After the cells were centrifuged (at 14,000 rpm, at a radius of 5.4 cm, at 4° C. for 10 minutes), the supernatant is collected. An equal volume of 2× sample buffer (0.1 M Tris-HCl, pH 6.8, 1% SDS, 5% β-mercaptoethanol, 10% glycerol, and 0.02% BPB) is added to the supernatant, and the mixture is allowed to stand at room temperature for 30 minutes.

The step of determining the phosphorylation state of Unc119 may be performed by measuring the level of phosphorylation of Unc119 by a known method. For example, the level of phosphorylation of Unc119 may be measured by electrophoresis capable of separating the phosphorylated form and the non-phosphorylated form, or may be measured by addition of ATP having a labeled phosphate group to the solution, or may be measured using an antibody that recognizes the phosphorylation of Unc119. Specifically, Phos-tag SDS-PAGE (the name of a product produced by FUJIFILM Wako Pure Chemical Corporation), $^{32}$P-labeled ATP (PerkinElmer, and others), anti-phosphorylated serine antibody (abcam, product code: ab9332), etc. can be used.

The step of selecting a test substance capable of enhancing the phosphorylation state of Unc119 as compared with the phosphorylation state of Unc119 in the absence of contact with the test substance may be performed by comparing the level of phosphorylation of Unc119 in samples contacted with each of a plurality of test substances (test substance groups) with that in a sample not contacted with the test substances (control group) and selecting a test substance capable of increasing the level of phosphorylation of Unc119. The degree of increase in the level of phosphorylation of Unc119 by the selected test substance is not limited to a particular one, but, for example, the test substance may increase the level of phosphorylation of Unc119 to 120% or more, 130% or more, 140% or more, 150% or more, 170% or more, 180% or more, 190% or more, or 200% or more as compared with that in a sample not contacted with the test substance.

The screening method of the present invention may comprise the steps of:

contacting each of a plurality of test substances with calcineurin, calmodulin and Unc119, determining the level of interaction between calcineurin and Unc119, and 1selecting a test substance capable of reducing the level of interaction between calcineurin and Unc119 as compared with the level of interaction between calcineurin and Unc119 in the absence of contact with the test substance.

The step of contacting each of a plurality of test substances with calcineurin, calmodulin and Unc119 in this embodiment may be performed by preparing a solution containing calcineurin, calmodulin and Unc119 and adding each of test substances to the solution, or alternatively, immobilizing Unc119 on a surface and adding calcineurin, calmodulin and each of test substances. The reaction conditions, including the amounts of calcineurin, calmodulin and Unc119 used, the amount of each of a plurality of test substances added, the solution, the temperature of the solution, and the duration of the contact are as described above.

The step of determining the level of interaction between calcineurin and Unc119 may be performed by measuring the level of interaction between calcineurin and Unc119 by a known method. Specifically, the level of interaction may be measured by, for example, FRET (fluorescence resonance energy transfer), Alphascreen (amplified luminescence proximity homogeneous assay), immunoprecipitation, ELISA, or the like.

The step of selecting a test substance capable of reducing the level of interaction between calcineurin and Unc119 as compared with the level of interaction between calcineurin and Unc119 in the absence of contact with the test substance may be performed by comparing the level of interaction between calcineurin and Unc119 in samples contacted with each of a plurality of test substances (test substance groups) with that in a sample not contacted with the test substances (control group) and selecting a test substance capable of reducing the level of interaction. The degree of reduction in the level of interaction between calcineurin and Unc119 by the selected test substance is not limited to a particular one, but, for example, the test substance may reduce the level of interaction between calcineurin and Unc119 to 90% or less, 80% or less, 70% or less, 60% or less, 50% or less, 40% or less, or 30% or less as compared with that in a sample not contacted with the test substance.

The screening method of the present invention may comprise the step of selecting a substance capable of activating CK2. In an embodiment where the substance capable of activating CK2 is a substance capable of enhancing the phosphorylation state of a substrate for CK2, the screening method of the present invention may comprise, for example, the steps of:

contacting each of a plurality of test substances with CK2 and a substrate for CK2 in the presence of ATP, determining the phosphorylation state of the substrate, and selecting a test substance capable of enhancing the phosphorylation state of the substrate as compared with the phosphorylation state of the substrate in the absence of contact with the test substance.

The substrate for CK2 may be any one selected from known substrates for CK2. Examples of the substrate for CK2 include, but are not limited to, BRD4 (bromodomain containing 4), and KBTBD8 (ketch repeat and BTB domain containing 8). Preferably, the substrate for CK2 is Unc119, which is a target protein of Klh118, a ubiquitinating enzyme predominantly expressed in the retina. The screening method of the present invention according to an embodiment where the substrate for CK2 is Unc119 will be described in detail below, but the screening method using a substrate other than Unc119 can also be performed in the same manner as described below.

The screening method of the present invention may comprise the steps of:

contacting each of a plurality of test substances with CK2 and Unc119 in the presence of ATP, determining the phosphorylation state of Unc119, and selecting a test substance capable of enhancing the phosphorylation state of Unc119 as compared with the phosphorylation state of Unc119 in the absence of contact with the test substance.

The step of contacting each of a plurality of test substances with CK2 and Unc119 in the presence of ATP may be performed by preparing a solution containing CK2, Unc119 and ATP and adding each of test substances to the solution, or alternatively, culturing cells expressing CK2 and Unc119 in culture medium containing ATP and adding each of test substances to the culture medium.

Unc119 that is appropriately used in the screening method of the present invention may be recombinant Unc119 produced by a known genetic engineering technique, as described above.

CK2 used in the screening method of the present invention may be from any organism, and may be from a mammal. Examples of the mammal include humans, chimpanzees, monkeys, dogs, cattle, mice, rats, and guinea pigs. Preferred is human CK2. CK2 may be recombinant CK2 that is commercially available as a reagent, or recombinant CK2 produced by a known genetic engineering technique.

CK2 exhibits its activity in the form of a heterotetramer composed of catalytic α subunits (a or a') and regulatory 0 subunits (β). The heterotetramer may be any of ααββ, αα'ββ and α'α'ββ. Accordingly, CK2-expressing cells can be prepared by introducing, into host cells, two genes: one is a gene encoding an a subunit and the other is a gene encoding a β subunit; or two genes: one is a gene encoding an α' subunit and the other is a gene encoding a β unit; or three genes: one is a gene encoding an α subunit, one is a gene encoding an α' subunit, and another one is a gene encoding a β subunit. The prepared CK2-expressing cells are cultured, and the culture supernatant or the cell extract is purified by a known method (for example, using an affinity column) to produce recombinant CK2.

The accession Nos. of the amino acid sequences of human CK2 α, α' and β subunits and the nucleotide sequences of the genes encoding the amino acid sequences are shown in Table 3. Information on the nucleotide sequences and amino acid sequences of CK2 of organisms other than humans is available from known databases (DDBJ, GenBank, EMBL, etc.).

TABLE 3

| Subunit | Gene name | Nucleotide sequence | Amino acid sequence |
|---|---|---|---|
| α subunit (α) | CSNK2A1 | NM_001895 | NP_001886 |
| α subunit (α') | CSNK2A2 | NM_001896 | NP_001887 |
| β subunit (β) | CSNK2B | NM_001320 | NP_001311 |

The cells expressing CK2 and Unc119 used in the screening method of the present invention may be cells expressing endogenous CK2 and endogenous Unc119, cells expressing recombinant CK2 and recombinant Unc119 each of which is derived from a transgene, or cells expressing CK2 and Unc119 each of which may be an endogenous or recombinant protein. Preferred are cells expressing recombinant CK2 and recombinant Unc119. The cells can be prepared by co-introducing a gene encoding CK2 and a gene encoding Unc119 into host cells. Specifically, the cells can be prepared by co-introducing a gene encoding a CK2 α subunit (α), a gene encoding a CK2 β subunit (β) and a gene encoding Unc119; or co-introducing a gene encoding a CK2 α subunit (α'), a gene encoding a CK2 β subunit (β) and a gene encoding Unc119; or co-introducing a gene encoding a CK2 α subunit (α), a gene encoding a CK2 α subunit (α'), a gene encoding a CK2 β subunit (β) and a gene encoding Unc119. The host cells are as exemplified above.

In the step of contacting each of a plurality of test substances with CK2 and Unc119 in the presence of ATP, wherein a solution containing CK2, Unc119 and ATP is prepared and each of test substances is added to the solution, the amounts of CK2 and Unc119 added to the solution are not limited to particular ones, but the molar ratio of CK2 and Unc119 may be about 1:1. The amount of ATP added is not limited to a particular one, and may be 10 μM to 1000 μM. The amount of each of test substances added is not limited and may be any amount that allows determination of the phosphorylation state of Unc119 in the subsequent step. Each of test substances may be added at varying concentrations within a predetermined range.

The solution used is not limited and may be any known buffer that can appropriately be used for phosphorylation reaction of a protein. The buffer may be, for example, 1× NEBuffer for Protein Kinase (NEB) containing 40 μM ATP. The reaction conditions including the temperature of the solution and the duration of the contact may be any conditions that allow CK2 to catalyze the phosphorylation of Unc119. For example, the temperature of the solution may be 30° C., and the duration of the contact may be 30 minutes.

In the step of contacting each of a plurality of test substances with CK2 and Unc119 in the presence of ATP, wherein cells expressing CK2 and Unc119 are cultured in culture medium containing ATP, and each of test substances is added to the culture medium, the amount of ATP added is not limited to a particular one, and may be 10 μM to 1000 μM. Each of test substances added to the culture medium may be in any amount that does not significantly inhibit proliferation of the cells and expression of the recombinant proteins. Each of test substances may be added at varying concentrations within a predetermined range. The duration of contact of each of test substances with the cells is not limited, and may be about 0.5 hours to about 48 hours.

In an embodiment where cells expressing CK2 and Unc119 are used, a cell lysate is prepared for measurement of the level of phosphorylation of Unc119 and used in the subsequent step. The cell lysate may be prepared by any method selected from known methods as appropriate. Specifically, the cell lysate may be prepared by the procedure as exemplified above.

The step of determining the phosphorylation state of Unc119 may be performed by measuring the level of phosphorylation of Unc119 by a known method. For example, the level of phosphorylation of Unc119 may be measured by electrophoresis capable of separating the phosphorylated form and the non-phosphorylated form, or may be measured by addition of ATP having a labeled phosphate group to the solution, or may be measured using an antibody that recognizes the phosphorylation of Unc119. Specifically, Phos-tag SDS-PAGE (the name of a product produced by FUJIFILM Wako Pure Chemical Corporation), $^{32}P$-labeled ATP (PerkinElmer, and others), anti-phosphorylated serine antibody (abcam, product code: ab9332), etc. can be used.

The step of selecting a test substance capable of enhancing the phosphorylation state of Unc119 as compared with the phosphorylation state of Unc119 in the absence of contact with the test substance may be performed by comparing the level of phosphorylation of Unc119 in samples contacted with each of a plurality of test substances (test substance groups) with that in a sample not contacted with the test substances (control group) and selecting a test substance capable of increasing the level of phosphorylation of Unc119. The degree of increase in the level of phosphorylation of Unc119 by the selected test substance is not limited to a particular one, but, for example, the test substance may increase the level of phosphorylation of Unc119 to 120% or more, 130% or more, 140% or more, 150% or more, 170% or more, 180% or more, 190% or more, or 200% or more as compared with that in a sample not contacted with the test substance.

The present invention also includes the following.

(a) A method for improving or preventing a symptom relating to a retina and/or light reception, the method comprising administering to a mammal an effective amount of a substance capable of maintaining or enhancing the phosphorylation state of Unc119.

(b) A substance capable of maintaining or enhancing the phosphorylation state of Unc119 for use in improvement or prevention of a symptom relating to a retina and/or light reception.

(c) Use of a substance capable of maintaining or enhancing the phosphorylation state of Unc119 in production of a medicament for improving or preventing a symptom relating to a retina and/or light reception.

The substance capable of maintaining or enhancing the phosphorylation state of Unc119 used in the above aspects (a), (b) and (c) of the invention may be a calcineurin inhibitor or a casein kinase 2 activator, and the calcineurin inhibitor may be ciclosporin or tacrolimus.

The symptom relating to a retina and/or light reception in the above aspects (a), (b) and (c) of the invention may be at least one disease selected from the group consisting of age-related macular degeneration, retinitis pigmentosa, Leber congenital amaurosis, Stargardt disease, cone-rod dystrophy, diabetic retinopathy, macular edema, retinal ischemia, retinal artery occlusion, retinal vein occlusion, photosensitive seizure, photosensitive epilepsy, psychiatric disorders, photic maculopathy, asthenopia, retinal dysfunction, sleep disorders, migraine and light-induced damage.

EXAMPLES

The present invention will be described in more detail below with reference to Examples, but the present invention is not limited thereto.

Example 1: Light-Induced Damage Experiment in Mice with Administration of Inhibitor of Calcineurin Activity (1) Light-Induced Damage Experimental Method For dark adaptation, BALB/c mice aged 4 weeks (Japan SLC, Inc.) were housed in the dark for 12 hours. Eight hours after the start of dark adaptation, tacrolimus (FK506, abcam) (dose: 10 mg/kg) or ciclosporin (Cyclosporine A, abcam) (dose: 100 mg/kg) was subcutaneously injected in the middle region of the back of the mice in the dark. For control mice, DMSO was administered. Mydriatic eye drops, Cyplegin (Santen Pharmaceutical Co., Ltd.), were administered in the dark 30 minutes before completion of dark adaptation. The mice were placed in a box with four mirrored walls and a mirrored floor, and exposed to blue light from a blue LED light. The wavelength of the blue LED light was about 450 nm, and the light reaching the mice was about 7000 lx. After exposure to blue light for 3 hours, the mice were housed under normal light conditions (about 30 lx light from fluorescent lamps) for 9 hours. This dark/light cycle repeated as one cycle for 6 days. In other words, administration of the drug and exposure to blue light (3 hours) were performed every day for 6 days to induce light-induced damage.

(2) Histological Analysis (a) Immunofluorescence Staining

On the next day following the last exposure to blue light, the mice were euthanized and the eyes were harvested. The specimens were fixed in 4% paraformaldehyde/PBS (phosphate buffer saline) at room temperature for 5 minutes. The specimens were then washed with PBS, and embedded in O.C.T. compound (Sakura Finetek). Retinal cryosections of 20 μm thick were sliced with a cryostat, mounted on glass slides, and dried at room temperature. The sections were washed twice with PBS, and blocked with blocking buffer (5% normal donkey serum and 0.1% TritonX-100 in PBS) at room temperature for 1 hour. The sections were reacted with primary antibodies at 4° C. overnight. The sections were washed three times with PBS, and reacted with secondary antibodies at room temperature for 2 hours. The primary antibodies used in this study were anti-Rhodopsin antibody (rhodopsin, rabbit polyclonal, Santa Cruz, 1:500 dilution), anti-S-opsin antibody (S-opsin (blue cone opsin), goat polyclonal, Santa Cruz, 1:500 dilution), and anti-M-opsin antibody (M-opsin (green cone opsin), rabbit polyclonal, Millipore, 1:500 dilution). The secondary antibodies used in this study were Alexa Flour 488-conjugated antibody (Thermo Fisher Scientific, 1:500 dilution), and Cy3-conjugated antibody (Jackson ImmunoResearch Laboratories, 1:500 dilution). After the completion of reaction with the secondary antibodies, the sections were washed three times with PBS and sealed in mounting medium. The nuclei staining with DAPI was also performed for all the specimens. All the fluorescence images were acquired under a confocal laser scanning microscope (LSM 700, Carl Zeiss).

(b) Measurement of Thickness of Photoreceptor Layer

Mouse retinal sections prepared in the same manner as above were washed twice with PBS, and the nuclei were stained with DAPI. The thickness of the photoreceptor layer was measured as the distance from the optic nerve. Specifically, the images were acquired under a confocal laser scanning microscope (LSM 700, Carl Zeiss), and the thickness of the photoreceptor layer was measured using the image analysis software Metamorph (Molecular Devices).

(3) Results of Tacrolimus Administration (a) Immunofluorescence Staining

Figure 2:
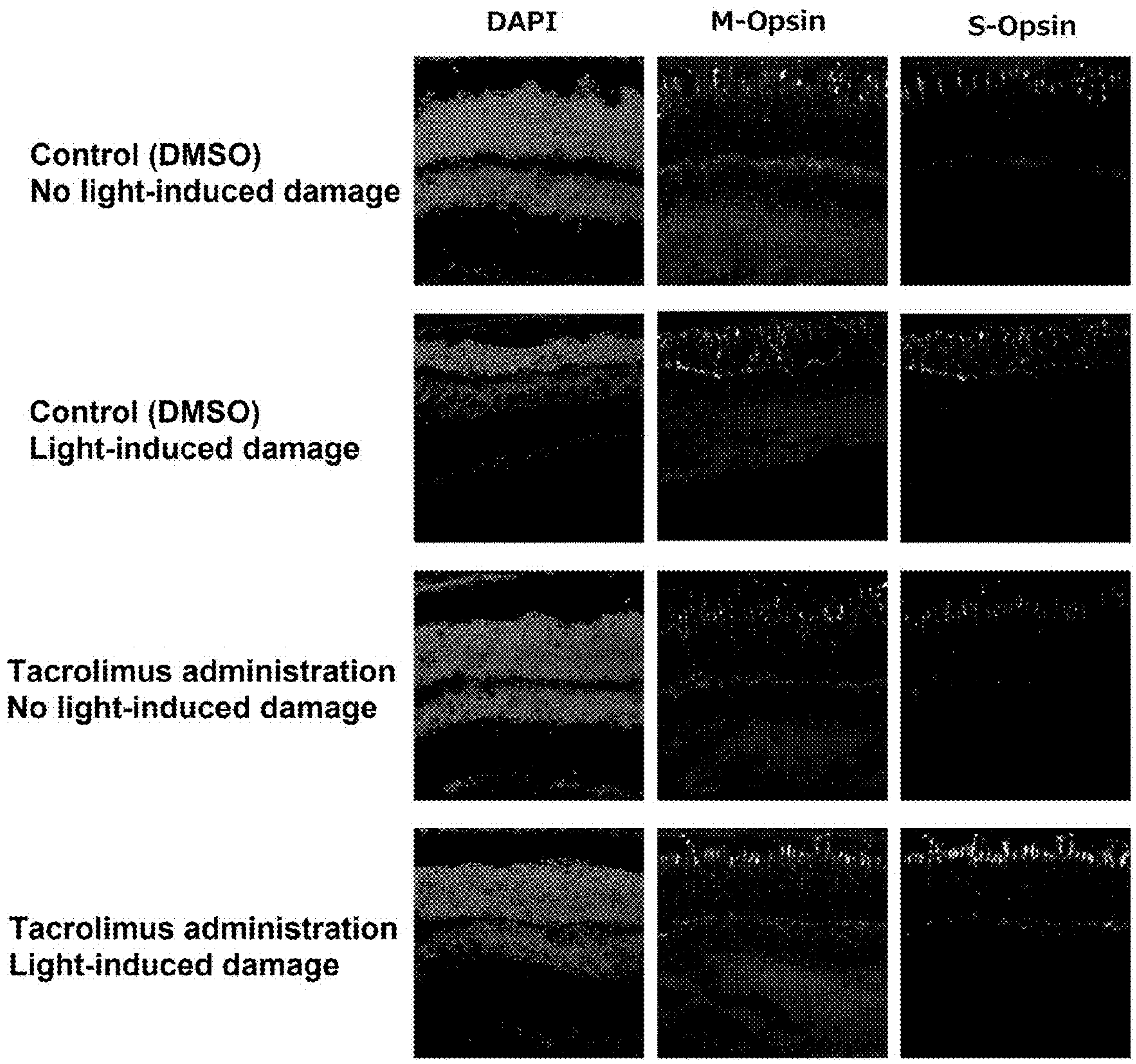
FIG. 2 shows fluorescence immunostaining of cone photoreceptor cells in the retina of tacrolimus-administered mice with light-induced damage.

The images of the photoreceptor layer of the retina of the mice that received tacrolimus are shown in FIGS. 1 and 2. FIG. 1 shows the outer segment of the rod photoreceptor cells stained with the anti-Rhodopsin antibody. FIG. 2 shows the cone photoreceptor cells stained with the anti-S-opsin antibody and the anti-M-opsin antibody. As apparent from FIG. 1, the control mice with light-induced damage (DMSO administration) developed damage to the outer segment of the rod photoreceptor cells. In contrast, in the tacrolimus-administered mice with light-induced damage, the structure of the outer segment of the rod photoreceptor cells was maintained and comparable to that of control mice without light-induced damage or tacrolimus-administered mice without light-induced damage. Also as apparent from FIG. 2, the control mice with light-induced damage (DMSO administration) developed damage to the cone photoreceptor cells. In contrast, in the tacrolimus-administered mice with light-induced damage, the structure of the cone photoreceptor cells was maintained and comparable to that of control mice without light-induced damage or tacrolimus-administered mice without light-induced damage.

(b) Measurement of Thickness of Photoreceptor Layer

Figure 3:
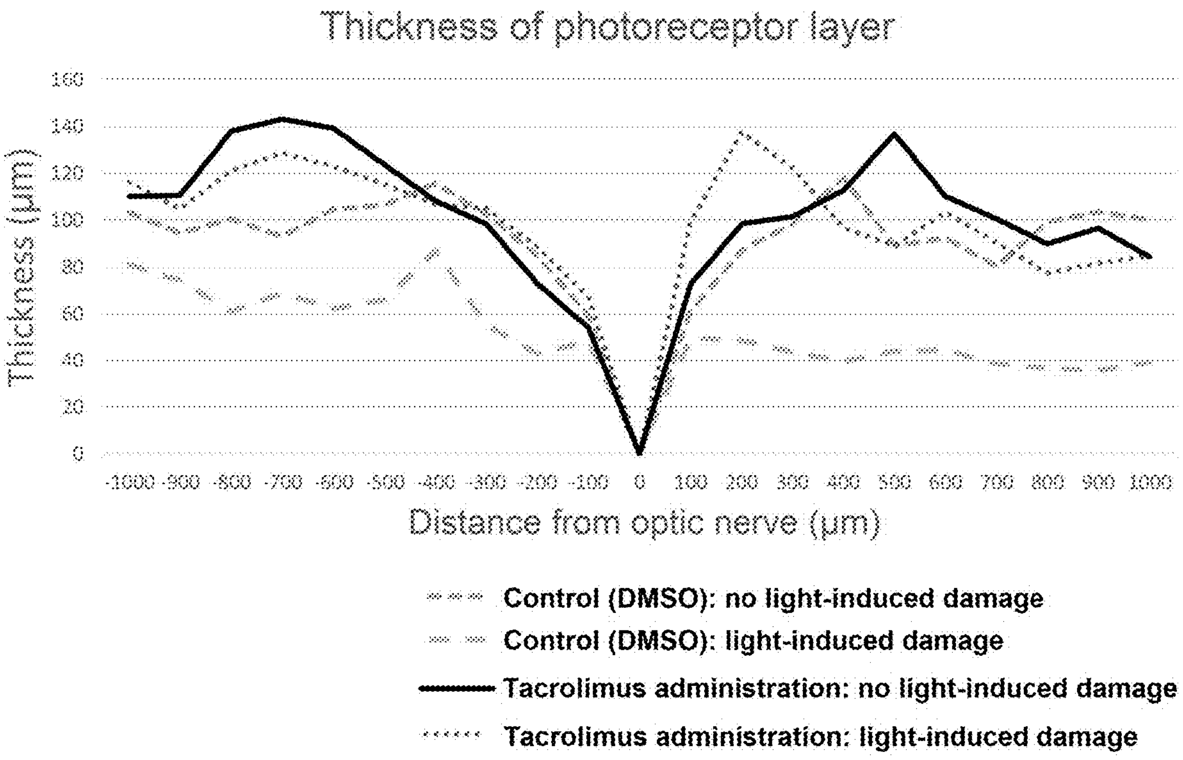
FIG. 3 shows the thickness of the photoreceptor layer of the retina of tacrolimus-administered mice with light-induced damage.

The thickness of the photoreceptor layer of the retina measured in the mice that received tacrolimus is shown in FIG. 3. As apparent from FIG. 3, significant reduction in the thickness of the photoreceptor layer was observed in the control mice with light-induced damage (DMSO administration). In contrast, in the tacrolimus-administered mice with light-induced damage, the thickness of the photoreceptor layer was maintained and comparable to that of control mice without light-induced damage or tacrolimus-administered mice without light-induced damage.

The results demonstrate that tacrolimus administration inhibits the degeneration of photoreceptor cells due to light exposure and maintains the structure of photoreceptor cells.

(4) Results of Ciclosporin Administration (a) Immunofluorescence Staining

Figure 4:
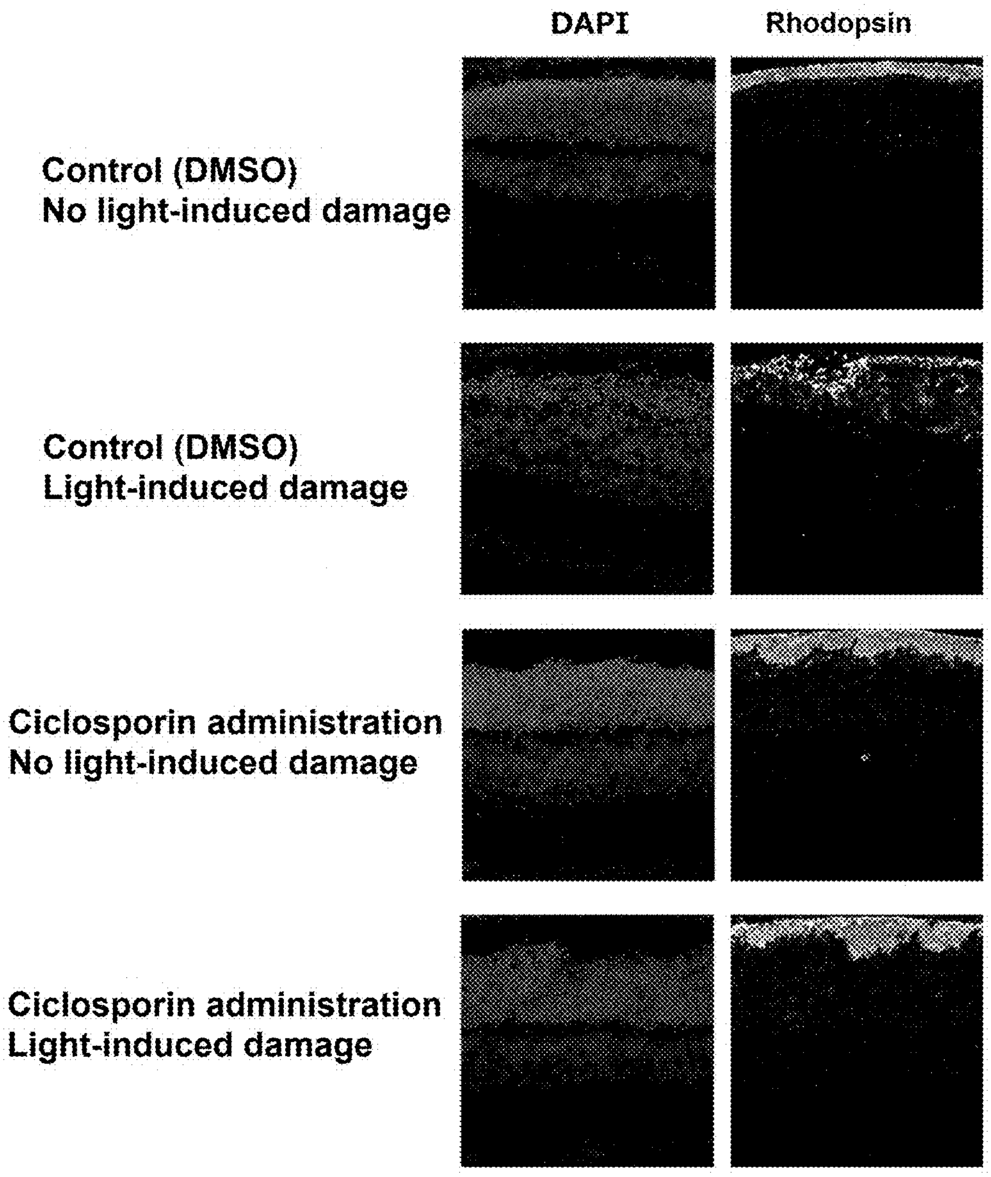
FIG. 4 shows fluorescence immunostaining of the outer segment of rod photoreceptor cells in the retina of ciclosporin-administered mice with light-induced damage.
Figure 5:
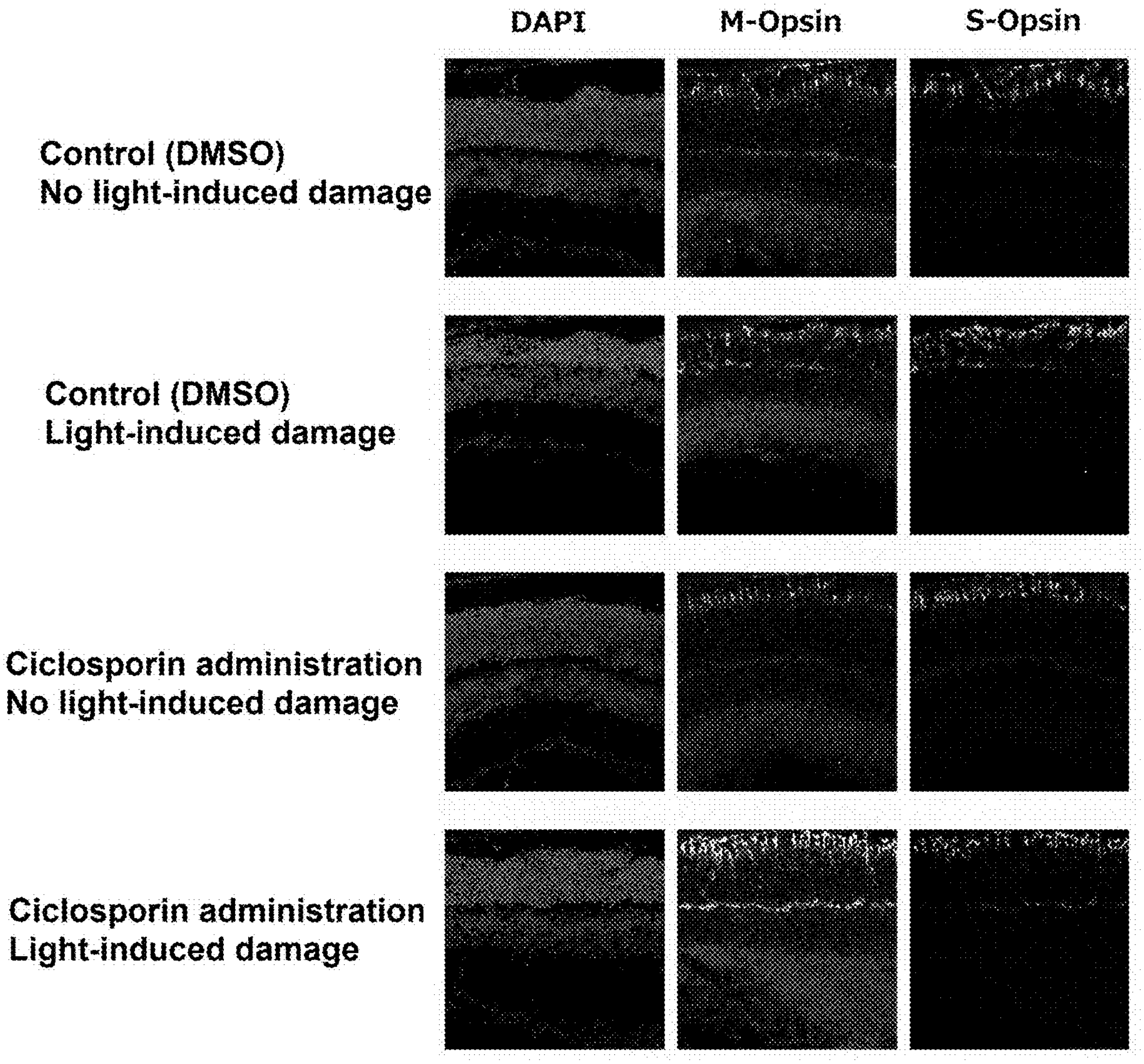
FIG. 5 shows fluorescence immunostaining of cone photoreceptor cells in the retina of ciclosporin-administered mice with light-induced damage.

The images of the photoreceptor layer of the retina of the mice that received ciclosporin are shown in FIGS. 4 and 5. FIG. 4 shows the outer segment of the rod photoreceptor cells stained with the anti-Rhodopsin antibody. FIG. 5 shows the cone photoreceptor cells stained with the anti-S-opsin antibody and the anti-M-opsin antibody. As apparent from FIG. 4, the control mice with light-induced damage (DMSO administration) developed damage to the outer segment of the rod photoreceptor cells. In contrast, in the ciclosporin-administered mice with light-induced damage, the structure of the outer segment of the rod photoreceptor cells was maintained and comparable to that of control mice without light-induced damage or ciclosporin-administered mice without light-induced damage. Also as apparent from FIG. 5, the control mice with light-induced damage (DMSO administration) developed damage to the cone photoreceptor cells. In contrast, in the ciclosporin-administered mice with light-induced damage, the structure of the cone photoreceptor cells was maintained and comparable to that of control mice without light-induced damage or ciclosporin-administered mice without light-induced damage.

(b) Measurement of Thickness of Photoreceptor Layer

Figure 6:
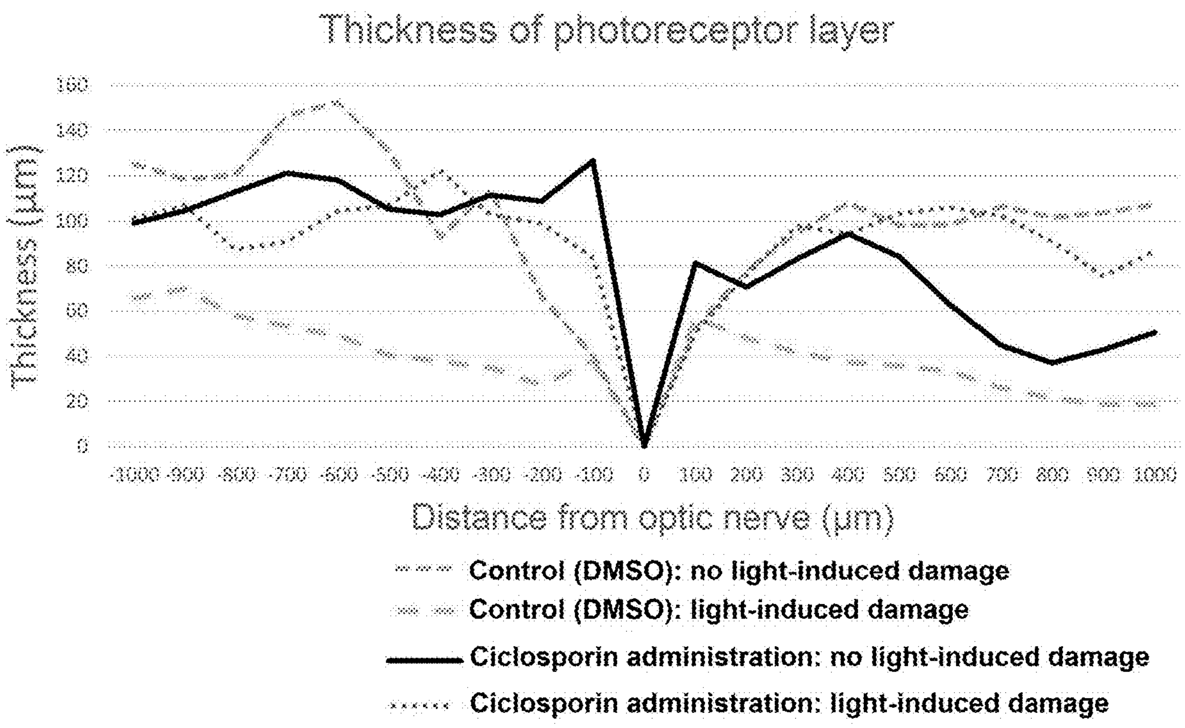
FIG. 6 shows the thickness of the photoreceptor layer of the retina of ciclosporin-administered mice with light-induced damage.

The thickness of the photoreceptor layer of the retina measured in the mice that received ciclosporin is shown in FIG. 6. As apparent from FIG. 6, significant reduction in the thickness of the photoreceptor layer was observed in the control mice with light-induced damage (DMSO administration). In contrast, in the ciclosporin-administered mice with light-induced damage, the thickness of the photoreceptor layer was maintained and comparable to that of control mice without light-induced damage or ciclosporin-administered mice without light-induced damage.

The results demonstrate that ciclosporin administration inhibits the degeneration of photoreceptor cells due to light exposure and maintains the structure of photoreceptor cells.

Example 2: Phosphorylation of Unc119 by Casein Kinase 2 (CK2)

(1) Preparation of Unc119 Expression Plasmid

To construct a plasmid expressing N-terminal 6×His (6× histidine)-tagged human Unc119, a full-length cDNA fragment of human Unc119 was amplified by PCR using a human Unc119 clone purchased from PlasmID (HsCD00330844) as a template, and subcloned into the pET-28b vector (Novagen).

(2) Expression and Purification of 6×His-Tagged Unc119

The 6×His-tagged Unc119 protein was expressed in *Escherichia coli* (strain BL21 (DE3)) and purified. The *E. coli* cells transduced with pET-28b-Unc119 were grown in LB medium to an $OD_{600\ nm}$ of 0.6, followed by treatment with 1 mM IPTG. The cells were cultured at 25° C. for 3 hours and 30 minutes and harvested by centrifugation. Harvested cells were lysed in sonication buffer (20 mM Tris-HCl, pH 7.4, 1 mM EDTA, 150 mM NaCl, 1% TritonX-100, 1 mM DTT, 50 mM imidazole, 1 mM PMSF, 2 μg/ml leupeptin, 5 μg/ml aprotinin, and 3 μg/ml pepstatin A) and centrifuged. The supernatants were mixed with Ni-NTA Agarose (QIAGEN) at 4° C. for 2 hours. The beads were washed with wash buffer (20 mM Tris-HCl, pH 7.4, 1% NP-40, 150 mM NaCl, and 5 mM EDTA), and eluted with elution buffer (200 mM imidazole, 150 mM NaCl, 20 mM Tris-HCl, pH 7.4, 0.1% TritonX-100, and 1 mM DTT).

(3) In Vitro Kinase Assay

Two micrograms of the purified 6×His-tagged Unc119 protein was reacted in 1× NEBuffer for Protein Kinase (NEB) containing 50 units of CK2 (NEB) and 40 μM ATP at 30° C. for 30 minutes. The reaction was terminated by addition of an equal volume of 2× sample buffer (0.1 M Tris-HCl, pH 6.8, 1% SDS, 5% β-mercaptoethanol, 10% glycerol, and 0.02% BPB), followed by leaving to stand at room temperature for 30 minutes.

(4) Phos-Tag SDS-PAGE

The samples after the in vitro kinase assay were detected by SDS-PAGE using Phos-tag acrylamide (Wako) according to the manufacturer's instructions (Reference 1: Mol. Cell. Proteomics. 5(4): 749-757 (2006), and Reference 2: Proteomics 11 (2): 319-323 (2011)).

(5) Results

Figure 7:
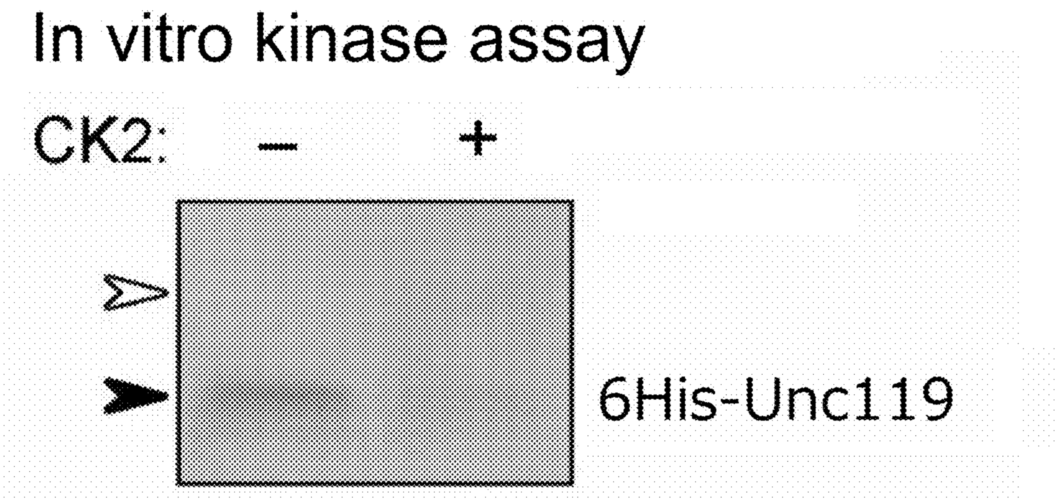
FIG. 7 shows the results of in vitro kinase assay demonstrating the phosphorylation of Unc119 by casein kinase 2.

The SDS-PAGE image is shown in FIG. 7. In the Phos-tag SDS-PAGE, a single band of the 6×His-tagged Unc119 protein (indicated by the black arrowhead) was observed in the sample that was not reacted with CK2, whereas an upshifted band (indicated by the white arrowhead) was observed in addition to the band indicated by the black arrowhead in the sample that was reacted with CK2, indicating the phosphorylation of Unc119 by CK2.

The present invention is not limited to each of the embodiments and Examples as described above, and various modifications are possible within the scope of the claims. Embodiments obtainable by appropriately combining the technical means disclosed in the different embodiments of the present invention are also included in the technical scope of the present invention. The contents of the scientific literature and the patent literature cited herein are hereby incorporated by reference in their entirety.

The invention claimed is:

1. A method for treating a symptom by maintaining or enhancing the phosphorylation state of Unc119 in a retina, the method comprising administering to a mammal in need thereof an effective amount of a calcineurin inhibitor, wherein the symptom is at least one retinal disease selected from the group consisting of dry age-related macular degeneration, retinitis pigmentosa, and Stargardt disease, and wherein the calcineurin inhibitor treats the symptom by maintaining or enhancing the phosphorylation state of Unc119.

2. The method according to claim 1, wherein the calcineurin inhibitor is ciclosporin or tacrolimus.

3. A method of inhibiting retinal degeneration by maintaining or enhancing the phosphorylation state of Unc119, the method comprising administering to a mammal in need thereof an effective amount of a calcineurin inhibitor, wherein inhibiting the retinal degeneration is slowing down retinal degeneration, wherein the retinal degeneration is caused by at least one disease associated with a dephosphorylation state of Unc119 selected from the group consisting of dry age-related macular degeneration, retinitis pigmentosa, and Stargardt disease, and wherein the calcineurin inhibitor inhibits the retinal degeneration by maintaining or enhancing the phosphorylation state of Unc119.

* * * * *